(12) United States Patent
Safari-Shad

(10) Patent No.: US 9,236,726 B2
(45) Date of Patent: Jan. 12, 2016

(54) METHODS FOR PROVIDING GENERATOR STATOR WINDING GROUND FAULT PROTECTION

(71) Applicant: Alliant Energy Corporate Services, Inc., Madison, WI (US)

(72) Inventor: Nader Safari-Shad, Madison, WI (US)

(73) Assignee: Alliant Energy Corporate Services, Inc., Madison, WI (US)

( * ) Notice: Subject to any disclaimer, the term of this patent is extended or adjusted under 35 U.S.C. 154(b) by 266 days.

(21) Appl. No.: 13/971,433

(22) Filed: Aug. 20, 2013

(65) Prior Publication Data

US 2014/0055889 A1   Feb. 27, 2014

Related U.S. Application Data

(60) Provisional application No. 61/691,471, filed on Aug. 21, 2012.

(51) Int. Cl.
| | |
|---|---|
| *G05B 11/01* | (2006.01) |
| *H02H 7/06* | (2006.01) |
| *A61B 1/12* | (2006.01) |

(52) U.S. Cl.
CPC ................... *H02H 7/06* (2013.01); *A61B 1/123* (2013.01); *A61B 1/125* (2013.01)

(58) Field of Classification Search
CPC ................... G05B 19/404; G05B 2219/41036; G05D 3/122; G05R 17/02
USPC ......................................... 318/629, 632, 140
See application file for complete search history.

(56) References Cited

U.S. PATENT DOCUMENTS

| | | | | |
|---|---|---|---|---|
| 2,309,487 | A | * | 1/1943 | Warrington ............ H02H 3/286 361/47 |
| 3,728,618 | A | * | 4/1973 | Nimes ...................... H02H 3/50 324/510 |

(Continued)

OTHER PUBLICATIONS

Adaptive Ground Fault Protection Schemes for Turbo-Generator Based on Third Harmonic Voltages; by Yin, Malik, Hope and Chen; IEEE Transactions on Power Delivery, vol. 5, No. 2, Apr. 1990.

(Continued)

*Primary Examiner* — Rina Duda
(74) *Attorney, Agent, or Firm* — Simmons Perrine Moyer Bergman PLC

(57) ABSTRACT

The present invention includes a method for providing ground fault protection to a generator. The method includes determining the existing state of the generator and second, determining the updated alarm or trip conditions of a relay connected to the generator in view of the existing state of the generator. This includes estimating a ratio of the magnitude of the $3^{rd}$ harmonic neutral voltage to the magnitude of the $3^{rd}$ harmonic terminal voltage of a generator, along with calculating the residual $3^{rd}$ harmonic voltage from the estimated $3^{rd}$ harmonic ratio. From this, a comparison is made between the energy of the residual voltage with a fractional energy of the $3^{rd}$ harmonic neutral voltage. Based on this comparison, an alarm or trip condition is signaled when the energy of the residual voltage is greater than the fractional energy of the $3^{rd}$ harmonic neutral voltage. The invention further includes adaptive relays and systems utilizing the adaptive relays, along with methods of producing power using the adaptive relays.

6 Claims, 1 Drawing Sheet

(56) References Cited

U.S. PATENT DOCUMENTS

| | | | | |
|---|---|---|---|---|
| 4,608,619 | A * | 8/1986 | Bomer | B60L 3/00 318/434 |
| 6,577,487 | B2 * | 6/2003 | Gertmar | H02J 3/01 174/18 |
| 6,891,303 | B2 * | 5/2005 | Leijon | H01F 3/10 174/DIG. 14 |
| 7,253,634 | B1 * | 8/2007 | Kasztenny | H02H 1/0092 324/509 |
| 7,570,469 | B2 | 8/2009 | Guzman-Casillas et al. | |
| 7,719,285 | B2 * | 5/2010 | Johansson | H02H 3/17 318/434 |

OTHER PUBLICATIONS

Differential Protection Based on Zero-Sequence Voltages for Generator Stator Ground Fault; by Nengling and Stenzel; IEEE Transactions on Power Delivery, vol. 22, No. 1, Jan. 2007.

Adaptive 100% Stator Earth Fault Protection Based on Third Harmonic Voltage Measurement; by Brncic, Gajic, Roxenborg and Bengtsson; Relay Protection and Substation Automation of Modern EHV Power Systems (Moscow—Cheboksary, Sep. 10-12, 2007).

* cited by examiner

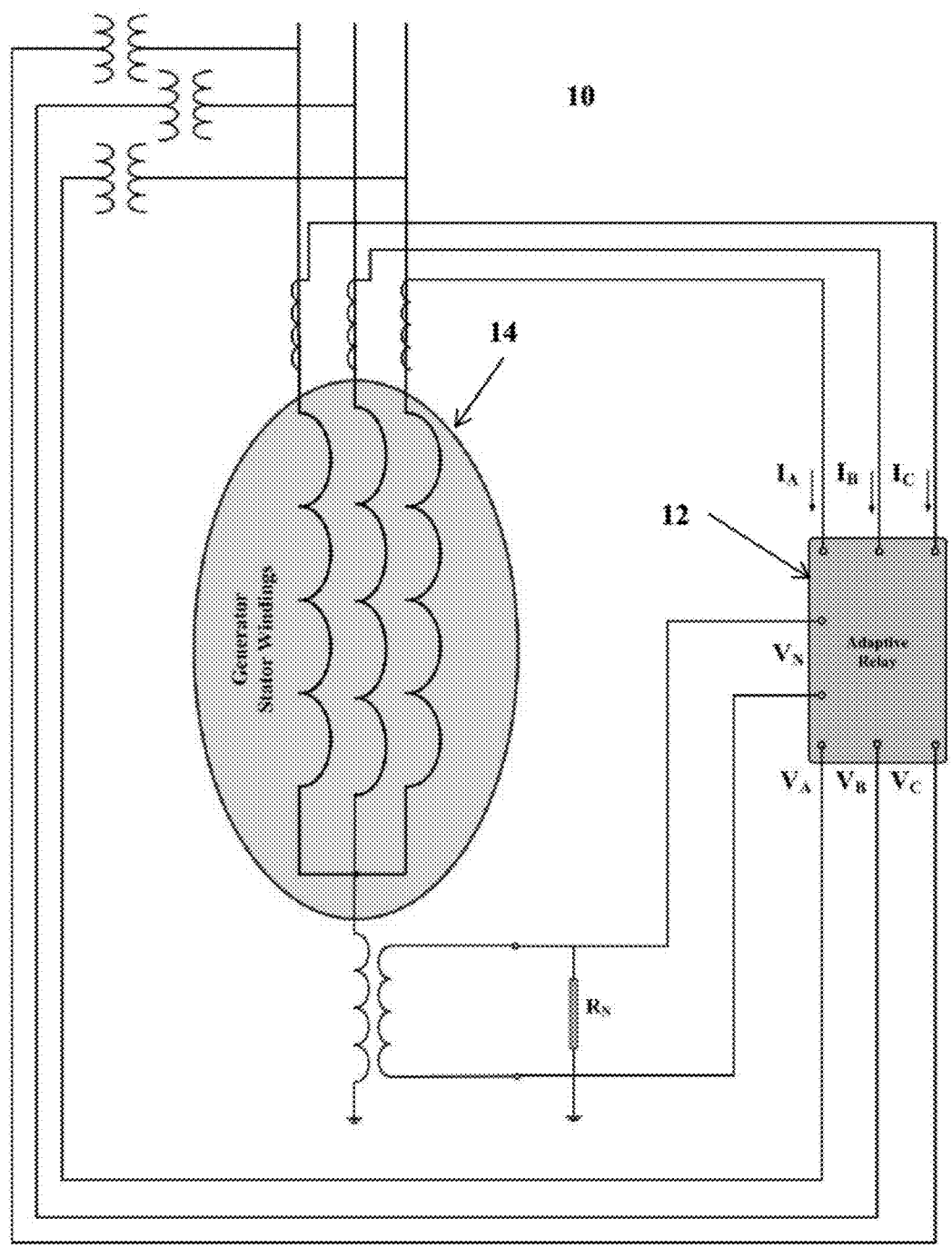

METHODS FOR PROVIDING GENERATOR STATOR WINDING GROUND FAULT PROTECTION

CLAIM OF PRIORITY

The present application claims the benefit of provisional application No. 61/691,471 filed on Aug. 21, 2012.

FIELD OF THE INVENTION

The present invention relates to improved methods, devices, and systems for providing ground fault protection for generators and more particularly methods, devices, and systems for providing 100% stator ground fault protection for synchronous generators.

BACKGROUND OF THE INVENTION

Synchronous generators operate within electrical systems to provide uninterrupted power to consumers. A variety of methods are used to protect the generator and thereby the electrical system from internal and external faults. Internal faults in the generator, such as stator winding ground faults, are an important concern to generation utilities worldwide.

One known system and method for 100% stator ground fault protection uses generator 3rd harmonic voltages. In this system and method, operating data from an in-use generator and the larger electrical system are collected and analyzed to set fixed settings into a relay in order to provide stator ground fault protection. These fixed relay settings determine when the relay is to trip or issue an alarm. The fixed relay settings must include extra tolerances (margins) to allow for normal 3rd harmonic voltage variations that occur while operating generators and electrical systems. Moreover, this solution cannot detect stator ground faults in an off-line generator prior to being connected to the electrical system because operating data is required to set the fixed relay settings.

Another known system and method utilizes sub-harmonic voltage injection. However, sub-harmonic voltage injection requires additional equipment to be placed into service, which requires field commissioning. And yet the system and method still require fixed relay settings. Furthermore, the total capacitance-to-ground of the generator stator windings, bus work, and delta-connected transformer windings of the unit transformer windings must be known to ensure the relay settings are correctly determined. Due to higher cost and maintenance of the added equipment, this solution is less attractive compared to the first solution. However, in contrast to the first solution, this solution can detect stator ground faults in an off-line generator prior to being connected to the electrical system.

In addition, known 100% stator ground fault protection systems and methods using 3rd harmonic voltages lack security at low power factors and during unusual power system conditions. Security means the degree of certainty that a protective relay will operate correctly for normal operating conditions of protected equipment. This lack of security causes false tripping or false alarms for the relays and leads to shutdown of the generator, which in turn leads to a costly loss of production and costly testing of the generator. Hence, it is desirable to develop a secure, low-cost stator ground fault protection methods, devices, and systems.

The present invention overcomes one or more of these problems.

SUMMARY OF THE INVENTION

The present invention includes a method for providing ground fault protection to a generator. The method includes determining the existing state of the generator and second, determining the updated alarm or trip conditions of a relay connected to the generator in view of the existing state of the generator. This includes estimating a ratio of the magnitude of the $3^{rd}$ harmonic neutral voltage to the magnitude of the $3^{rd}$ harmonic terminal voltage of a generator, along with calculating the residual $3^{rd}$ harmonic voltage from the estimated $3^{rd}$ harmonic ratio. From this, a comparison is made between the energy of the residual voltage with a fractional energy of the $3^{rd}$ harmonic neutral voltage. Based on this comparison, an alarm or trip condition is signaled when the energy of the residual voltage is greater than the fractional energy of the $3^{rd}$ harmonic neutral voltage. The invention further includes adaptive relays and systems utilizing the adaptive relays, along with methods of producing power using the adaptive relays.

BRIEF DESCRIPTION OF THE FIGURE

FIG. 1 shows a schematic drawing of the system of the present invention.

DETAILED DESCRIPTION

The present invention includes methods of providing 100% stator ground fault protection to generators in general and synchronous generators in particular. The methods allow a relay to adapt to the existing state of the generator to which the relay is connected or to the state of the electrical system to which the generator is connected. The inventive devices (e.g. the adaptive relays) incorporate these methods and the inventive systems incorporated these devices.

Numerous outside factors can influence the state of the generator including the load on the generator, the load on the electrical system, voltage spikes and drops, power swings, etc. Detecting ground faults in the stator winding is difficult in the ever changing state of the generator. So having a better understanding of the instantaneous state of the generator or electrical system is needed. From the state of the generator or electrical system, updated or adaptive alarm or trip conditions can be set on the relay for the generator. In this manner, the generator is protected even while the existing state of the generator and electrical system is taken into account. Recognize that the existing state of the generator takes into account both internal and external influences, such as from the electrical system to which the generator is connected.

The ground fault protection method of the present invention accomplishes these two goals. First, it determines the existing state of the generator and second, it determines the updated alarm or trip conditions of the relay in view of the existing state of the generator. The first goal is accomplished by estimating a ratio of the magnitudes of the $3^{rd}$ harmonic neutral and terminal voltages and then calculating a residual voltage from the estimated ratio. The second goal is accomplished by comparing the energy of the residual $3^{rd}$ harmonic voltage with the fractional energy of the $3^{rd}$ harmonic neutral voltage. Based on this comparison, the existence of an alarm or trip condition is determined and an alarm or trip signal will issue.

Initially, an estimate of the ratio of the magnitudes of the $3^{rd}$ harmonic voltages of the generator is needed. This estimate is a snap shot of the existing state of the generator. This estimate is in contrast to the direct calculation of the ratio of the magnitudes of the $3^{rd}$ harmonic voltages. The estimated ratio ($\hat{\rho}$) is the ratio of the magnitude of the $3^{rd}$ harmonic neutral voltage ($\tilde{V}_{N3}$) of the generator to the magnitude of the $3^{rd}$ harmonic terminal voltage ($\tilde{V}_{T3}$) of the generator, that is, $$\hat{\rho} = \frac{\tilde{V}_{N3}}{\tilde{V}_{T3}}.$$

The estimated $3^{rd}$ harmonic ratio is preferred over the directly calculated $3^{rd}$ harmonic ratio because the estimated $3^{rd}$ harmonic ratio is less susceptible to measurement and numerical noise and thus leads to a ground fault protection scheme and relay that are more secure.

Any of several iterative techniques are suitable for estimating the $3^{rd}$ harmonic ratio including weighted least-squares (WLS) and recursive weighted least-squares (RWLS). A RWLS with a 'forgetting factor' is preferred (also know as Exponentially-Weighted-Past RWLS or EWP-RWLS). Likewise, use of a Kalman adaptive filter (KAF) may also be used. Each of these techniques is well understood by a skilled artisan and outlined below.

The ratio ($\hat{\rho}$) may be estimated using a weighed least squares technique. The ratio may be estimated using the following vector equation:

$\hat{\rho}_{WLS} = [X^T W X]^{-1} X^T W Y$ (eq. 1), where X is the matrix of $\tilde{V}_{T3}$ at time 1 to M, $X^T$ is the transposed matrix X, Y is the matrix of $\tilde{V}_{N3}$ at time 1 to M, and W is an M by M matrix of the scalar positive weights associated with each error (e(i)). The error (e(i)) is incurred due to noise, disturbance, or simply model mismatches at the $i^{th}$ data point.

The weighted least squares ratio ($\hat{\rho}$) may also be estimated using the following scalar equation:

$$\hat{\rho}_{WLS} = \left[\sum_{i=1}^{M} w(i)\tilde{V}_{T3}^2(i)\right]^{-1} \left[\sum_{i=1}^{M} w(i)\tilde{V}_{T3}(i)\tilde{V}_{N3}(i)\right], \quad \text{(eq. 2)}$$

where w(i) is scalar positive weights associated with each error (e(i)).

The ratio ($\hat{\rho}$) may also be estimated using a recursive weighed least squares technique. The ratio may be estimated using the following algorithm:

$$RWLS \text{ Algorithm} \begin{cases} \hat{\rho}_{WLS}(t) = \hat{\rho}_{WLS}(t-1) + K(t)v(t), & \text{(eq. 3)} \\ \quad i.c. = \hat{\rho}_0 > 0, \\ v(t) = \tilde{V}_{N3}(t) - \tilde{V}_{T3}(t)\hat{\rho}_{WLS}(t-1), \\ K(t) = P(t)w(t)\tilde{V}_{T3}(t), \\ P(t) = P(t-1) - \dfrac{P(t-1)w(t)\tilde{V}_{T3}^2(t)P(t-1)}{1 + P(t-1)w(t)\tilde{V}_{T3}^2(t)}, \\ \quad i.c. = \prod_0 > 0, \\ w(t) = \dfrac{1}{PF(t)^2 + \delta}, \quad \delta > 0. \end{cases}$$

Here, PF(t) is the power factor. i.c. is short for initial conditions, $\hat{\rho}_0$ is an initial guess for the value of the ratio, $\Pi_0$ is the degree of confidence in this guess. A Small $\Pi_0$ indicates high confidence while large $\Pi_0$ indicates little confidence in the chosen $\hat{\rho}_0$. The residual voltage v(t) is the predicted parameter estimation error at time t. It is the difference between $\tilde{V}_{N3}(t)$ and its one-step-ahead prediction $\tilde{V}_{T3}(t) \hat{\rho}_{WLS}(t-1)$. Small v(t) implies that $\hat{\rho}_{WLS}(t-1)$ is good and very little correction is needed. The gain K(t) determines how much v(t) should change the parameter estimate $\hat{\rho}_{WLS}(t-1)$. The constant δ is chosen to ensure that the weights are large, but finite during low power factor operating points.

The ratio ($\hat{\rho}$) may also be estimated using an exponentially weighted past recursive weighed least squares technique. The ratio may be estimated using the following algorithm:

$$EWP - RWLS \text{ Algorithm} \qquad \text{(eq. 4)}$$

$$\begin{cases} \hat{\rho}_{EWP}(t) = \hat{\rho}_{EWP}(t-1) + K(t)v(t), \\ \quad i.c. = \hat{\rho}_0 > 0, \\ v(t) = \tilde{V}_{N3}(t) - \tilde{V}_{T3}(t)\hat{\rho}_{EWP}(t-1), \\ K(t) = P(t)w(t)\tilde{V}_{T3}(t), \\ P(t) = \lambda^{-1}\left[P(t-1) - \dfrac{P(t-1)w(t)\tilde{V}_{T3}^2(t)P(t-1)}{\lambda + P(t-1)w(t)\tilde{V}_{T3}^2(t)}\right] \\ \quad i.c. = \prod_0 > 0, \\ w(t) = \dfrac{1}{PF(t)^2 + \delta}, \quad \delta > 0. \end{cases}$$

The variables and constants in this algorithm have the same definitions as in the RWLS algorithm. The difference between the RWLS estimate of the ratio and the EWP-RWLS estimate of the ratio lies in λ in the determination of P(t). λ is between 0 and 1 and is the 'forgetting factor'; that is, λ represents an exponential decaying of earlier and earlier weighted errors (w(t)). When λ=1, then the RWLS and EWP-RWLS equations become equal; that is, there is no decaying of earlier weighted errors.

In addition to the techniques discussed above, the ratio ($\hat{\rho}$) may also be estimated using a Kalman adaptive filter (KAF). The adjective adaptive is added to the Kalman filter to indicate the difference between the conventional Kalman filter where the system parameters are time-invariant or perhaps time varying, but known in advance. The ratio may be estimated using the following KAF algorithm:

$$KAF \text{ Algorithm} \qquad \text{(eq. 5)}$$

$$\begin{cases} \hat{\rho}_{KAF}(t) = \hat{\rho}_{KAF}(t-1) + K(t)v(t), \\ \quad i.c. = \hat{\rho}_0 > 0, \\ v(t) = \tilde{V}_{N3}(t) - \tilde{V}_{T3}(t)\hat{\rho}_{KAF}(t-1), \\ K(t) = P(t)w(t)\tilde{V}_{T3}(t), \\ P(t) = P(t-1) - \dfrac{P(t-1)w(t)\tilde{V}_{T3}^2(t)P(t-1)}{1 + P(t-1)w(t)\tilde{V}_{T3}^2(t)} + N \\ \quad i.c. = \prod_0 > 0, \\ w(t) = \dfrac{1}{PF(t)^2 + \delta}, \quad \delta > 0. \end{cases}$$

The variables and constants in this algorithm have the same definitions as in the RWLS algorithm. The difference between the KAF estimate of the ratio and the RWLS estimate of the ratio lies in the addition of N in the determination of P(t). The addition of N to the equation prevents P(t) from converging to zero as time t gets large, and is the reason that the adaptation period in the KAF never stops. N plays a similar role to the forgetting factor λ in the EWP-RWLS technique.

With the estimated $3^{rd}$ harmonic ratio, the residual $3^{rd}$ harmonic voltage (v) is calculated. The traditional calculation of the residual $3^{rd}$ harmonic voltage is $v(t)=\tilde{V}_{N3}(t)-\tilde{V}_{T3}(t)\rho(t-t_{cc})$ (eq. 6), where $\rho(t-t_{cc})$ is the directly calculated ratio of $\tilde{V}_{N3}$ to $\tilde{V}_{T3}$. By substituting in the estimated ratio, $\hat{\rho}(t-1)$, the calculation of the residual $3^{rd}$ harmonic voltage becomes less susceptible to measurement and numerical noises. Thus, the update calculation for the residual $3^{rd}$ harmonic voltage is: $v(t)=\tilde{V}_{N3}(t)-\tilde{V}_{T3}(t)\hat{\rho}(t-1)$ (eq. 7).

The residual $3^{rd}$ harmonic voltage represents the estimated balance between the distribution of the $3^{rd}$ harmonic voltage magnitudes at the neutral versus at the terminal. This estimated balance is an accurate estimate of this distribution throughout the entire operating range of the generator since $\hat{\rho}$ is constantly updated. And thus, gives an accurate estimate of the existing state of the generator or electrical system.

Now that an understanding of the existing state of the generator (as it may have been influenced by the electrical system) is achieved, the alarm or trip conditions of the relay need to be updated. The alarm or trip conditions are essentially monitoring whether the operate quantity of a relay is larger than the restraint quantity of the relay over a plurality of data points. This is expressed as a comparison of the two quantities.

The traditional comparison is given by $|\tilde{V}_{N3}(t)-\tilde{V}_{T3}(t)\rho(t-t_{cc})|>\beta\tilde{V}_{N3}(t)$ (eq. 8) and uses the residual $3^{rd}$ harmonic voltage using the directly calculated ratio of the $3^{rd}$ harmonic voltages and compares it to a fractional portion of the $3^{rd}$ harmonic neutral voltage. A better comparison is given by $|\tilde{V}_{N3}(t)-\tilde{V}_{T3}(t)\hat{\rho}(t-1)|>\beta\tilde{V}_{N3}(t)$ (Eq. 9), where the estimated ratio of $3^{rd}$ harmonic voltages is used in place of the directly calculated ratio. In both equations, $\beta$ is a user selected constant between 0 and 1 that gives a fractional portion of the $3^{rd}$ harmonic neutral voltage. $\beta$ is selected to modify the sensitivity of comparison calculation. The left side of eq. 9 is the operate quantity and the right side of eq. 9 is the restraint quantity.

When eq. 9 is true, then the alarm or trip condition will exist, and an alarm or trip signal will issue. Stated alternatively, when the operate quantity is greater than the restraint quantity, an alarm or trip signal will be issued by the relay.

This comparison is consistent. That is, for a ground fault at or near the neutral, $\tilde{V}_{N3}$ is approximately 0 and $\tilde{V}_{T3}$ will be approximately equal to the total $3^{rd}$ harmonic voltage magnitude. Thus, eq. 9 will collapse down to $|\tilde{V}_{N3}(t)\hat{\rho}(t-1)|>0$. Thus, the operate quantity will be greater than the restraint quantity, and an alarm or trip will exist. Thus, this permits the detection of ground faults at or near the neutral of the generator. Moreover, this trip or alarm condition will exist as estimated ratio, $\hat{\rho}(t-1)$ gradually decays to zero.

Also, this comparison permits the detection of ground faults at start up. That is, by setting the starting condition to $\hat{\rho}(0)=1$ in eq. 9, the operate quantity will be greater than the restraint quantity.

To improve the security of the ground fault detection scheme, the comparison is carried out multiple times using multiple readings of the $3^{rd}$ harmonic voltages. These several data points are used to compare energies. That is, energies are calculated from several instantaneous readings of the $3^{rd}$ harmonic residual and neutral voltages (as shown below). This smoothes out the readings by reducing the impact of any individual instantaneous reading. Thus, the comparison of energies is done with at least three and preferably a minimum of six data points before an alarm or trip condition exists or is signaled.

The operate quantity of the energy is defined as:

$$\mathcal{J}_{AO}(t) = \begin{cases} 0, & \text{if } 1 \leq t \leq L \\ \sum_{s=t-L}^{t} |v(s)|^2, & \text{if } t > L, \end{cases} \quad (\text{eq. 10)},$$

where L is the number of instantaneous readings (i.e. data points) and preferably L is at least six. The restraint quantity is defined as:

$$\mathcal{J}_{AR}(t) = \begin{cases} \sum_{s=1}^{t} \tilde{V}_{N3}^2(s), & \text{if } 1 \leq t \leq L \\ \sum_{s=t-L}^{t} \tilde{V}_{N3}^2(s), & \text{if } t > L. \end{cases} \quad (\text{eq. 11})$$

These two quantities, representing energies, are compared:

$\mathcal{J}_{AO}(t)>\beta\mathcal{J}_{AR}(t)$ (eq. 12), and an alarm or trip is signaled if this equation is satisfied for any $t>L$. Note that the window of the L samples is needed to ensure that the adaptive ratio estimation algorithm has properly learned the current operating conditions of the generator or electrical system. Moreover, depending on the timing of a fault which occurs after the learning period is completed, an alarm or trip signal is issued, if over a finite window of L samples, the energy of the residual signal $v(t)$ is strictly greater than the fraction of the energy of $\tilde{V}_{N3}$.

The present invention also includes devices, called adaptive relays that carry out the invention method. The adaptive relay includes a processor, which in turn is programmable. Programming of the processor permits the alarm or trip conditions of the relay to be modified on a real time basis; that is, the trip or alarm conditions for the relay can be continuously adjusted to meet the existing state of the generator and the electrical system. The continuously adjusted relay settings provide a secure and dependable protection to the generator. Exemplary programmable relays include SEL-300G and SEL-700G relays.

Essentially, the processor in the relay is programmed to carry out the methods discussed above; namely, determining the existing state of the generator and electric system and then updating the alarm or trip conditions of the relay.

In addition to the adaptive relay, the present invention also relates to systems that incorporate the adaptive relay, as shown in FIG. 1; in particular, those systems 10 in which one or more adaptive relays 12 are electrically connected to a generator 14.

The method of operating the generator includes producing power with a generator having an adaptive relay electrically connected to the generator.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "or" should be understood to include by the conjunctive and disjunctive definitions of the word. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method for providing 100% stator ground fault protection to a generator, comprising:
   estimating a ratio of the magnitude of the $3^{rd}$ harmonic neutral voltage to the magnitude of the $3^{rd}$ harmonic terminal voltage of a generator,
   calculating the residual $3^{rd}$ harmonic voltage from the estimated $3^{rd}$ harmonic ratio, comparing an energy of the residual voltage with a fractional energy of the $3^{rd}$ harmonic neutral voltage, and
   signaling an alarm or trip condition when the energy of the residual voltage is greater than the fractional energy of the $3^{rd}$ harmonic neutral voltage.

2. The method of claim 1 wherein the signaling step further comprises signaling an alarm or trip condition when the energy of the residual voltage is greater than the fractional energy of the $3^{rd}$ harmonic neutral voltage for at least six consecutive comparisons.

3. The method of claim 1 wherein the estimating step comprises an iterative technique to estimate the ratio of the magnitude of the $3^{rd}$ harmonic neutral voltage and the magnitude of the $3^{rd}$ harmonic terminal voltage.

4. The method of claim 3 wherein the iterative technique is selected from recursive weighted least-squares (RWLS), exponentially-weighted-past RWLS (EWP-RWLS) or a Kalman adaptive filter (KAF).

5. A system for providing ground fault protection to a generator, comprising:
   an adaptive relay electrically connected to a generator, where the relay is programmed to determine an existing state of an generator or electrical system by:
   estimating a ratio of the magnitude of the $3^{rd}$ harmonic neutral voltage to the magnitude of the $3^{rd}$ harmonic terminal voltage of a generator,
   calculating the residual $3^{rd}$ harmonic voltage from the estimated $3^{rd}$ harmonic ratio,
   comparing an energy of the residual voltage with a fractional energy of the $3^{rd}$ harmonic neutral voltage, and
   signaling an alarm or trip condition when the energy of the residual voltage is greater than the fractional energy of the $3^{rd}$ harmonic neutral voltage.

6. A method of operating a generator, comprising:
   producing power with a generator having an adaptive relay that is electrically connected to the generator, wherein the adaptive relay is programmed to:
   establish the existing state of the generator or electrical system;
   calculate a residual $3^{rd}$ harmonic voltage; and
   modify, in real time, the alarm or trip conditions of the relay based on the residual $3^{rd}$ harmonic voltage; and
   signal an alarm or trip when the modified alarm or trip conditions of the adaptive relay are violated.

* * * * *